United States Patent [19]

Rohrbach et al.

[11] 4,415,656

[45] Nov. 15, 1983

[54] INCREASING THE STABILITY OF AMYLOGLUCOSIDASE

[75] Inventors: Ronald P. Rohrbach, Forest Lake; Mary J. Maliarik, Lake Forest, both of Ill.

[73] Assignee: UOP Inc., Des Plaines, Ill.

[21] Appl. No.: 380,797

[22] Filed: May 21, 1982

[51] Int. Cl.$^3$ .......................... C12P 19/20; C12N 9/34
[52] U.S. Cl. ........................................ 435/96; 435/205
[58] Field of Search .................................. 435/96, 205

[56] References Cited
U.S. PATENT DOCUMENTS 3,592,734  7/1971  Kroyer .............................. 435/96 X
3,783,100  1/1974  Larson et al. ..................... 435/96 X

OTHER PUBLICATIONS

Eyring & Magee, *J. Cell. and Comp. Physiol.* 20, 169, (1942).
Millar, Grafius, Wild & Palmer, *Biophysical Chemistry*, 2, 189, (1974).
Miyagawa and Suzuki, *Arch. Biochem. Biophys.*, 105, 297, (1964).

*Primary Examiner*—Lionel M. Shapiro
*Attorney, Agent, or Firm*—James R. Hoatson, Jr.; Eugene I. Snyder; William H. Page, II

[57] ABSTRACT

Thermal deactivation of amyloglucosidase is substantially retarded at elevated pressures relative to atmospheric pressure. The productivity of glucose formation from amyloglucosidase-catalyzed hydrolysis of starch or partially hydrolyzed starch is significantly increased when the hydrolysis is performed at a pressure greater than about 500 psig.

4 Claims, No Drawings

INCREASING THE STABILITY OF AMYLOGLUCOSIDASE

BACKGROUND OF THE INVENTION

The present utilization of enzymes to effect commercial processes is of considerable importance, and future utilization almost certainly will increase. One reason why enzymatic conversions are advantageous is their chemical specificity. Another advantage of enzymatic reactions is their relatively modest energy requirements. Still another advantage they possess is that their environmental impact is minimal relative to traditional chemical processes.

The desirability of commerical enzymatic processes has been an impetus for the development of immobilized enzyme systems. A homogeneous enzymatic process necessarily is performed batchwise and the enzyme usually is discarded because it is generally difficultly separable from reactants and products. This results in increased expense both because enzymes generally are an expensive material component of the process and because a batch process is usually more costly than a continuous one. In immobilized enzyme systems, the enzyme is "fixed" to solid support, thereby insolubilized. Although enzyme reactivity may be altered relative to a homogeneous enzyme process, the advantage of enzyme reuse far outweighs reduced enzyme activity. Additionally an immobilized enzyme system generally permits continuous processes for enzyme catalyzed conversions using, for example, a fixed bed. Accordingly, enzyme immobilization has been an important advance in the art of commerical enzymatic conversions.

Even with improved utilization of enzymes via immobilization it is desirable to increase productivity of the enzyme. By productivity is meant the amount of product formed per unit of enzyme. Not only is it desirable to increase total productivity, it also may be commercially desirable to increase the productivity per unit time, sometimes even at the cost of lower total productivity, because of associated lower product cost. Both total productivity and productivity per unit time often are limited by thermal denaturation of the enzyme.

Thermal denaturation of an enzyme is a phenomenon whereby the enzyme loses its activity with passage of time through a temperature induced process. Thus, at any given temperature enzyme activity may decay exponentially with time, leading to a decrease in productivity over any given time period and limiting total productivity. A commonly used index of thermal deactivation is the half-life of the enzyme; the greater the half-life, the less the thermal deactivation, or reciprocally, the greater the stability.

Productivity per unit time is influenced by the process temperature because the rate of enzymatic conversion increases with temperature, hence the productivity per unit time also increases with temperature. However, at some point thermal denaturation of the enzyme becomes an important competing process and above some optimum temperature the productivity per unit time will decrease because of thermal deactivation of the enzyme.

Thus it is readily seen that thermal deactivation of enzymes is a serious limitation on productivity in commerical enzymatic conversions. Although thermal deactivation cannot be eliminated, apparent retardation or reduction of deactivation will have important benefits, and processes employing such a method of retardation or reduction will have substantial competitive advantages.

An object of this invention is to retard or reduce the thermal deactivation of glucoamylase or amyloglucosidase (AG). On the one hand, accomplishing this objective will lead to greater productivity in the enzyme process. More specifically, accomplishing the objective according to the invention herein leads to greater reactant conversion per unit of enzyme activity by substantially increasing the usable lifetime unit of the AG. On the other hand, accomplishing the objective can lead to a greater productivity per unit time by permitting the enzymatic process to be carried out at a higher temperature.

Increasing the total productivity and productivity per unit time are substantial advantages which will inhere to an enzyme process using the invention described herein. Our invention is based on the discovery that thermal deactivation AG is retarded at high pressure. The invention based thereon is a method of enzymatically hydrolyzing certain carbohydrates, particularly starch or partially hydrolyzed starch, at a pressure greater than about 500 psig.

Information related to the effect of pressure on thermal denaturation of enzymes is sparse. Eyring and Magee, *J. Cell. and Comp. Physiol.*, 20, 169 (1942) showed that increased pressure somewhat reduced the thermal deactivation of luciferase, a two-fold increase in stability being shown at 7000 psig relative to atmospheric pressure. In contrast, only one of three acetylcholinesterase sizeozymes was stabilized at high pressure against thermal denaturation, with less than a 50% increase in stability at 2000 psig. Millar, Grafius, Wild, and Palmer, *Biophysical Chemistry*, 2, 189 (1974). In further contrast, alpha-amylase (taka-amylase A) was shown to be denatured at high pressure, above about 80,000 psig. Miyagawa and Suzuki, *Arch. Biochem. Biophys.*, 105, 297 (1964).

The observations upon which the invention claimed herein is based are remarkable on several counts. First, it is unpredictable that an increase in pressure will cause stabilization of amyloglucosidase against thermal denaturation. Secondly, the magnitude of such stabilization is without precedent. In particular, we observed an increased stabilization of over 400% at only 3000 psig.

DESCRIPTION OF THE INVENTION

The invention herein is a method of increasing the productivity in the amyloglucosidase catalyzed hydrolysis of a 1,4-linked carbohydrate comprising contacting a solution of said carbohydrate with amyloglucosidase at a pressure greater than about 500 psig. The invention is based on the discovery that increased pressure retards or reduces thermal deactivation of amyloglucosidase. What is more surprising is the magnitude of the pressure effect on amyloglucosidase; thermal deactivation is retarded to such an extent that the half-life at 60° C. is increased by over 400% at 3000 psig relative to atmospheric pressure.

The process parameters of enzyme catalyzed reactions are generally confined to such variables as temperature and pH. Viewed from another perspective, the invention described embodies the discovery that pressure may also be an important process parameter, or independent variable, in an enzyme catalyzed process. Our invention is a method of increasing the productivity in AG catalyzed hydrolysis of suitable substrates. Because the most desired product of AG catalyzed conversions is glucose, in this disclosure productivity means the total amount of glucose formed per unit of initial activity of amyloglucosidase.

Any kind of amyloglucosidase may be used in this invention, although not necessarily with equivalent results. The AG may be fungal or bacterial in origin. Examples of fungi which are producers of AG include species from the genera Aspergillus, Talaromyces, Rhizopus, Monascus, Coniophora, Cephalosporium, Neurospora, Pennicillium, Mucor, Pericularia, Endomyces, Endomycopsis, Torula, and Schizophyllum. Examples of bacterial sources of AG include species of the genus Flavobacterium. Amoung the organisms which are particularly useful in the production of AG are *Aspergillus niger* and *Talaromyces duponti*.

The substrates which are hydrolyzed by AG and 1,4-linked carbohydrates. The most important examples of such a substrate are starch and partially hydrolyzed starch. Partially hydrolyzed starch, or thinned starch, may arise either from acid catalyzed partial hydrolysis of starch or by enzymatic thinning processes.

The amyloglucosidase and carbohydrate, preferably starch or partially hydrolyzed starch, are contacted under hydrolytic conditions at a pressure greater than about 500 psig. Substantial retardation of thermal deactivation may occur at pressures as high as about 10,000 psig. However, operational limitations make it more desirable to operate at an upper pressure limit of about 5,000 psig. Pressures in the range from about 1,000 to about 4,000 psig may be employed advantageously.

Other variables in the AG catalyzed hydrolysis of starch and partially hydrolyzed starch to glucose are not affected by the pressures used in this invention and, because these variables are well known, they need not be here repeated with great specificity. The temperature of hydrolysis generally is from about 40 up to about 65° C., depending upon the inherent thermal stability of the AG used. Where a thermophilic organism is the source of AG, the hydrolysis temperature may be substantially higher than 65° C. The pH is on the acidic side, generally from about 4 to about 6 with the optimum depending upon temperature, source of AG, feedstock, and so forth.

The invention described herein may be used both with soluble enzyme and immobilized AG. Where soluble AG is employed, a solution of the substrate, generally partially hydrolyzed starch, and a suitable amount of amyloglucosidase is adjusted to the proper pH with a buffer, such as phosphate. The solution is then brought to reaction temperature, which is between about 40° C. and about 65° C., and higher for AG from a thermophilic organism, and usually in the nieghborhood of 60° C., at a pressure greater than about 500 psig, generally from about 500 to about 10,000 psig. The hydrolysis is then permitted to continue until the desired glucose level, often greater than about 90%, is attained. Using the higher pressures described herein will permit the use of more starch or partially hydrolyzed starch per unit initial activity of amyloglucosidase used.

More desirably the enzyme is immobilized and the supported enzyme is used as a bed in a continuous operation. Both the support matrix used for immobilization of the enzyme and the method of immobilization are subject to broad diversity well known to the worker skilled in this art. For example, the immobilized enzyme system may be AG adsorbed on alumina or a resin, entrapped and/or cross-linked in a gel, attached to controlled-pore glass, or covalently bonded to a matrix of an inorganic oxide impregnated with a cross-linked polyamine bearing excess pendant functional groups. Immobilization may be performed by contacting the enzyme with the support material, and other reagents where necessary, for a time adequate for the enzyme to become bound to or immobilized on the matrix. For example, immobilized AG may be used as a fixed bed with a feedstock of starch or partially hydrolyzed starch, at an appropriate pH and temperature as described above, passed through the bed at a space velocity calculated to afford the desired conversion. In some cases conversions may be relatively low, for example, about 10–15%, and in other cases high conversions on the order of 90% or greater may be desired. The pressure under which the hydrolysis is effected is greater than about 500 psig and may be up to about 10,000 psig.

The example which follows serves merely to illustrate this invention and is not intended to limit it thereby.

EXAMPLE

An immobilized amyloglucosidase was prepared as follows. 1 g of 60/80-mesh alumina was mixed with 10 ml of a 1.8% aqueous solution of polyethylenimine at pH 10.5. The mixture was evacuated and degassed for 1 hr., then permitted to remain for 16 hrs. at room temperature. Excess liquid was removed by decantation and the solid was washed with two 10 ml portions of distilled water. The solid then was treated with 10 ml of a 5% aqueous solution of glutaraldeyde buffered with phosphate (0.05 molar) at pH 7.0. After 1 hr. excess liquid was removed by decantation, completing preparation of the support matrix. Amyloglucosidase from *Aspergillus niger* was immobilized by contacting the matrix with a solution at pH 3.5 containing about 145 units of enzyme per gram support matrix at room temperature for about 16 hrs. The excess enzyme solution is removed by decantation, the immobilized AG is washed well with water, and assayed.

Immobilized enzyme was assayed using 1.5 cc material packed into a plug flow reactor. Using partially hydrolyzed starch (Maltrin 150) as the feedstock at pH 4.2 and 60° C., the flow rate was maintained to keep conversion to glucose less than about 15% so as to eliminate film diffusion effects. Effluent was sampled periodically using a glucose analyzer, with the activity, A, calculated from the equation:

$$A = \frac{\text{glucose produced (g/ml)} \times \text{flow rate (ml/hr)}}{\text{immobilized } AG \text{ (g)}}$$

By this method it was determined that the immobilized AG had an initial acitivity of 81 units per gram.

A feedstock of partially hydrolyzed starch (Maltrin 150, DE 15), buffered with 0.05 molar acetate to pH 4.2 and containing 100 ppm sodium benzoate and 50 ppm sodium omadine, was supplied to 2 reactors maintained at 60° C. at a rate sufficient to keep the conversion below about 15%. The 2 reactors differed only in that one was operated at atmospheric pressure whereas the other was operated at about 3000 psig. It was determined that the half-life of immobilized AG when hydrolysis was conducted at 1 atmosphere was 5 days, whereas the half-life when the hydrolysis was conducted at 3000 psig was 22 days. Thus, an increase in stability of over 400% accompanies operation of the AG-catalyzed conversion at 3000 psig.

What is claimed is:

1. A method of increasing the productivity in amyloglucosidase-catalyzed hydrolysis of a 1,4-linked carbohydrate comprising contacting a solution of said carbohydrate with amyloglucosidase at a pressure greater than about 500 psig.

2. The method of claim 1 where the carbohydrate is starch or a partially hydrolyzed starch.

3. The method of claim 1 where the amyloglucosidase is of fungal or bacterial origin.

4. The method of claim 3 where the amyloglucosidase is produced by a member of a genus selected from the group consisting of Aspergillus, Talaromyces, Rhizopus, Monascus, Coniophora, Cephalosporium, Neurospora, Penicillium, Mucor, Pericularia, Endomyces, Endomycopsis, Torula, Schizophyllum and Flavobacterium.

* * * * *